United States Patent
Wagner et al.

(10) Patent No.: US 8,870,570 B2
(45) Date of Patent: Oct. 28, 2014

(54) CHUCKING DEVICE FOR A MEDICAL OR DENTAL HANDPIECE

(75) Inventors: Hannes Wagner, Salzburg (AT); Gunter Teufelberger, Bürmoos (AT); Josef Spitzauer, Oberndorf (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 127 days.

(21) Appl. No.: 13/318,778

(22) PCT Filed: May 7, 2010

(86) PCT No.: PCT/EP2010/056236
§ 371 (c)(1),
(2), (4) Date: Nov. 3, 2011

(87) PCT Pub. No.: WO2010/128131
PCT Pub. Date: Nov. 11, 2010

(65) Prior Publication Data
US 2012/0058446 A1 Mar. 8, 2012

(30) Foreign Application Priority Data
May 7, 2009 (EP) .................................. 09006196

(51) Int. Cl.
*A61C 3/00* (2006.01)
*A61C 3/02* (2006.01)
*A61C 1/14* (2006.01)
*A61C 1/12* (2006.01)

(52) U.S. Cl.
CPC ... *A61C 1/12* (2013.01); *A61C 3/02* (2013.01); *A61C 1/145* (2013.01)
USPC .......................................................... 433/147

(58) Field of Classification Search
USPC .................. 433/126–128, 146–149, 152–154, 433/159–163; 81/438, 177.1, 177.85; 279/23.1, 102, 103; 408/202, 203, 110; 606/79–85; 464/160–170; 148/573, 148/587; 384/31; 446/145; 451/375
See application file for complete search history.

(56) References Cited

U.S. PATENT DOCUMENTS 1,789,559 A * 1/1931 Meunier ........................... 81/54
3,762,732 A * 10/1973 Speed ........................... 279/102
(Continued)

FOREIGN PATENT DOCUMENTS

| DE | 3012240 | 10/1981 |
| EP | 0820734 | 1/1998 |
| JP | 7-255747 | 10/1995 |

OTHER PUBLICATIONS

International Search Report for PCT/EP2010/056236 (mailed Oct. 29, 2010).

(Continued)

*Primary Examiner* — Cris L Rodriguez
*Assistant Examiner* — Mirayda A Aponte
(74) *Attorney, Agent, or Firm* — Klarquist Sparkman, LLP

(57) ABSTRACT

A medical or dental handpiece includes a tool holding/releasing device with a hollow shaft, a first holding unit and a second holding unit. The hollow shaft can be put into a drive motion for holding a treatment tool. The hollow shaft extends along a central axis and has a tool receptacle opening. The second holding unit is separate from the first holding unit and axially offset from the first holding unit relative to the central axis. Both holding units are designed to axially secure a treatment tool held in the hollow shaft and to transmit a torque to the treatment tool. Both holding units have at least one shaped element each and a bore penetrating the outer wall of the hollow shaft. The shaped element can be held in such a way that it projects through the bore into the interior of the hollow shaft. A locking sleeve is operatively connected to the shaped elements and can move relative to the hollow shaft. The locking sleeve surrounds the hollow shaft and an operating element operatively connected to the locking sleeve for the movement or sliding of the locking sleeve.

31 Claims, 2 Drawing Sheets

(56) References Cited

U.S. PATENT DOCUMENTS

| | | | |
|---|---|---|---|
| 4,940,410 A * | 7/1990 | Apap et al. | 433/102 |
| 5,028,181 A * | 7/1991 | Jenkins et al. | 409/215 |
| 5,219,174 A * | 6/1993 | Zurbrugg et al. | 279/82 |
| RE35,147 E * | 1/1996 | Apap et al. | 433/102 |
| 5,584,689 A * | 12/1996 | Loge | 433/128 |
| 6,644,150 B2 * | 11/2003 | Chen | 81/438 |
| 6,722,667 B2 * | 4/2004 | Cantlon | 279/22 |
| 7,036,404 B2 * | 5/2006 | Liou | 81/438 |
| 7,565,854 B2 * | 7/2009 | Chiang et al. | 81/467 |
| 7,581,470 B1 * | 9/2009 | Huang | 81/438 |
| 7,740,249 B1 * | 6/2010 | Gao | 279/75 |
| 7,891,275 B2 * | 2/2011 | Huang | 81/438 |
| 8,172,236 B2 * | 5/2012 | Shibata | 279/143 |
| 2002/0151902 A1 | 10/2002 | Riedel et al. | |
| 2004/0173061 A1 * | 9/2004 | Liou | 81/177.85 |
| 2008/0190251 A1 * | 8/2008 | Huang | 81/438 |
| 2009/0107304 A1 * | 4/2009 | Chiang et al. | 81/429 |
| 2009/0188352 A1 * | 7/2009 | Huang | 81/438 |

OTHER PUBLICATIONS

Written Opinion for PCT/EP2010/056236 (mailed Oct. 29, 2010).

* cited by examiner

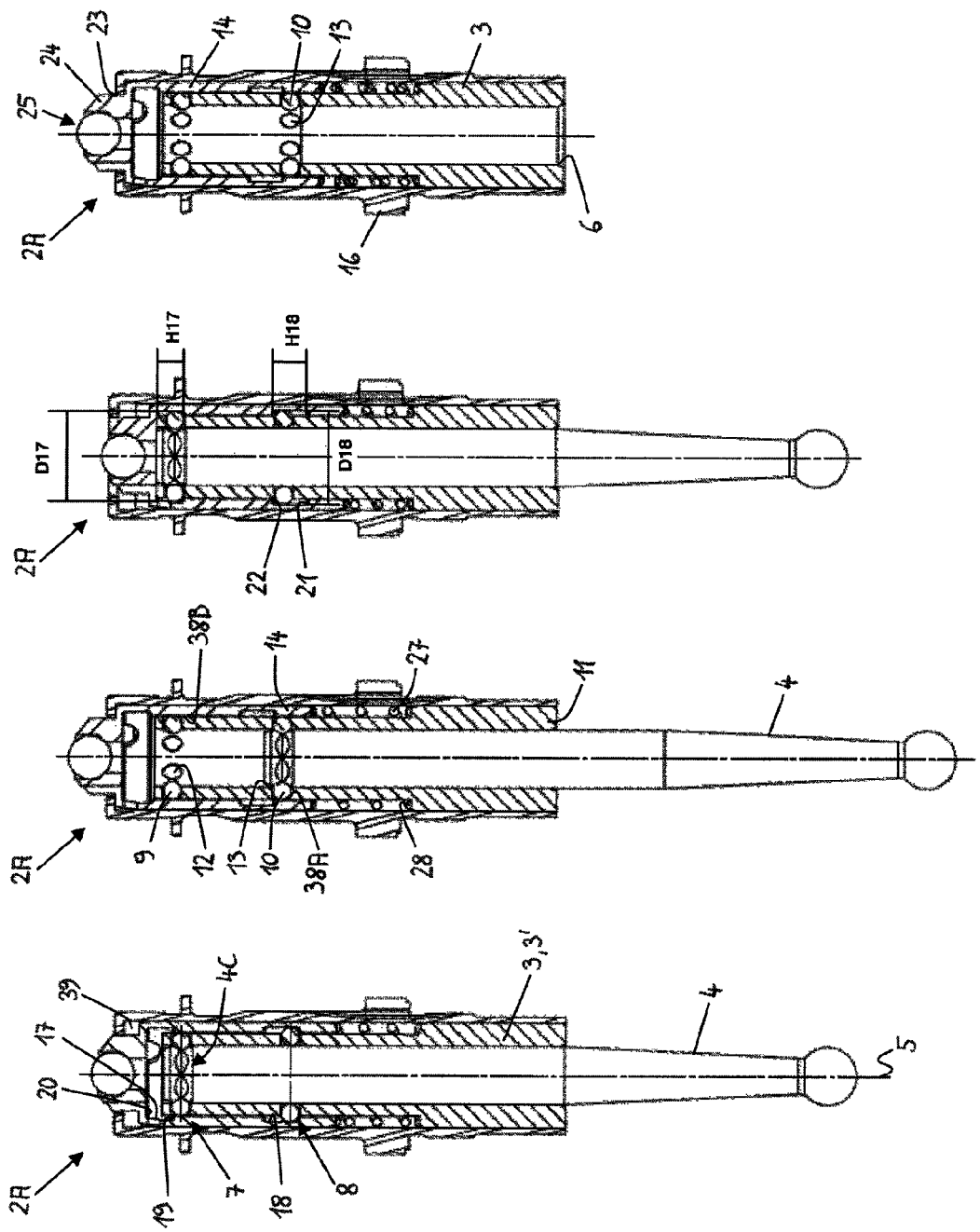

CHUCKING DEVICE FOR A MEDICAL OR DENTAL HANDPIECE

CROSS-REFERENCE TO RELATED APPLICATION

This application is the U.S. National Stage of PCT/EP2010/056236, filed on May 7, 2010, which claims the benefit of EP 09006196.1, filed May 7, 2009. These prior applications are incorporated herein by reference.

BACKGROUND

This application relates to a medical or dental handpiece with a clamping or chucking device.

A handpiece with such a chucking device is known, for example, from patent application US 2009/0220911 A1. The chucking device is designed to hold the tool at two different insertion depths, so that the length of that part of the tool that projects from the chucking device (and thus from the handpiece) can be altered. For this purpose, the chucking device has two independent sections offset from one another and arranged along the longitudinal axis: One elongate section located at the upper end of the chucking device, for transmission of torque to the tool and for the support and centering of the tool in the chucking device, and one radially spring-mounted section formed by spring shackles for the axial holding of the tool in the chucking device.

The disadvantage of this chucking device is that, particularly when the tool is in the position in which it projects further from the chucking device, only a very short end section of the shaft is held in the section for torque transmission, so that the tool is only insufficiently held and centered in the chucking device (see, for example, FIG. 11 of US 2009/0220911 A1). Thus particularly at high speeds there is a danger that the tool will not turn smoothly or will start to vibrate.

It would be advantageous to create a medical, particularly a dental, handpiece with a chucking device designed to hold the tool in two different insertion depths, wherein the tool, particularly in the position in which it projects further from the chucking device, is supported and centered better in the chucking device.

SUMMARY

According to an embodiment, a medical or dental handpiece is proposed that comprises a tool holding/releasing device with a hollow shaft that can be put into a drive motion for holding a treatment tool, wherein the hollow shaft extends along a central axis and has a tool receptacle opening, a first holding unit and a second holding unit separate from the first holding unit and axially offset from the first holding unit relative to the central axis, wherein both holding units are designed to axially secure a treatment tool held in the hollow shaft and to transmit a torque to the treatment tool, and wherein both holding units have at least one shaped element each and a bore penetrating the outer wall of the hollow shaft in which the at least one shaped element can be held in such a way that it projects through the bore into the interior of the hollow shaft, a locking sleeve operatively coupled with or operatively connected to the shaped elements that can move relative to the hollow shaft and that surrounds the hollow shaft and an operating element that works together with the locking sleeve to move or slide the locking sleeve.

Due to this configuration of the handpiece, in particular due to the two separate and offset holding units with their shaped elements and bores in the hollow shaft, it is possible to use the hollow shaft over its entire length for the support and centering of the treatment tool.

Preferably the two separate and offset holding units are substantially identical in structure.

The term handpiece comprises all straight or pistol-shaped handpieces or handles, curved handpieces or handles, which are often referred to as contra-angle handpieces in the dental field, as well as parts of handpieces, in particular a head section of a handpiece, which can be connected to detachable gripping sections, for example. The term handpiece is also understood to include both cordless handpieces, in particular those with a replaceable or chargeable power source, and handpieces comprising a power supply cable and a regulating unit, control unit and/or power supply unit connected thereto.

To improve the support and centering of the treatment tool still further, according to a preferred embodiment the hollow shaft is formed as a hollow cylindrical, preferably single-piece, shaft whose inner diameter is substantially constant over its entire length.

To provide particularly convenient and easy operation of the tool holding/releasing device, according to another embodiment the locking sleeve has on its inner side a first recess which is associated with the first holding unit and a second recess associated with the second holding unit, so that at least one shaped element of the first holding unit can be held in the first recess and at least one shaped element of the second holding unit can be held in the second recess.

According to a preferred embodiment, the first recess has a first shoulder located closer to the tool receptacle opening and a second shoulder located more distant from the tool receptacle opening, and the second recess has a third shoulder located closer to the tool receptacle opening and a fourth shoulder located more distant from the tool receptacle opening, wherein the distance between the first and third shoulders is greater than the distance between the center point of at least one shaped element of the first holding unit and the center point of at least one shaped element of the second holding unit. This ensures that regardless of whether a treatment tool is supported in the hollow shaft or not, or how deeply the treatment tool is inserted into the hollow shaft, the shaped elements are always sufficiently fastened in or on the bore of the hollow shaft associated with them.

According to another preferred embodiment, the first recess is located further from the tool receptacle opening than the second recess, wherein the diameter (through the hollow shaft) of the first recess is less than the diameter of the second recess. In this way, the at least one shaped element of the first recess projects further into the hollow shaft than the at least one shaped element of the second recess, so that the at least one shaped element of the first recess additionally serves as an axial stop for the treatment tool when the treatment tool is completely inserted into the hollow shaft.

According to another preferred embodiment, the axial height of the first and second recesses relative to the central axis is different, wherein preferably the axial height of the first recess located further from the tool receptacle opening is lower than the axial height of the second recess located closer to the tool receptacle opening.

According to another embodiment, the hollow shaft and the locking sleeve are surrounded by a bearing sleeve that has an opening on the end facing the operating element through which contact can be made between the locking sleeve and the operating element. A protrusion of the locking sleeve preferably projects through the opening in the bearing sleeve. Preferably, the protrusion of the locking sleeve has a spherical end facing the operating element, so that an essentially point-shaped contact can be made with the operating element. Due to the substantially point-shaped contact, the transmission of heat to the operating element and the associated risk of burning should the operating element come into contact with tissue is significantly reduced.

According to one embodiment, a drive element is provided on the bearing sleeve in order to place the hollow shaft into a drive motion. The drive element is, for example, implemented as a gearwheel, as a gear pinion, as a rotor or impeller driven by compressed gas or as part of an eccentric drive.

According to one embodiment, the locking sleeve is tensioned by a spring element that is supported on a shoulder provided on the outside of the hollow shaft or on a shoulder provided on the inner side of the hollow shaft, so that a particularly space-saving configuration of the tool holding/releasing device is obtained.

According to another embodiment, at least one shaped element of at least one holding unit is spherical in form or has a spherical end which faces the central axis of the hollow shaft. The at least one shaped element is, for example, implemented as a ball, a half-ball, an ellipsoid or as a cylinder with a spherical end.

In order to achieve uniform, reliable clamping or chucking of the tool in the hollow shaft, according to one embodiment multiple shaped elements per holding unit are provided that are arranged around the hollow shaft, particularly evenly spaced. The first holding unit and the second holding unit preferably each have three or six shaped elements. The three shaped elements in each case are preferably used in a handpiece driven by compressed gas in which lower torques are transmitted. For mechanically driven handpieces that are often designed to transmit higher torques and in which it is therefore advantageous to fasten the treatment tool more securely in the hollow shaft, for each holding unit preferably more than three shaped elements are used, with six shaped elements being particularly preferable.

According to one embodiment, the handpiece has a treatment tool with a treatment section and a shaft section, on which a single contact element is provided for selective contact with the at least one shaped element of the first holding unit or the second holding unit, wherein the contact element is located directly at that end of the shaft section that is furthest away from the treatment section. Thus, a treatment tool is provided in an advantageous manner that can be used both with the described tool holding/releasing device and with other known clamping or chucking devices, particularly with known force-fitting or non-positive chucking devices with radially spring-tensioned clamping straps that grip the treatment tool. The treatment tool can be attached to the handpiece releasably.

The part of the shaft section extending from the contact element towards the treatment section that can be held in the hollow shaft can have a substantially constant outer diameter, further improving the support and centering of the treatment tool.

The invention will now be explained below on the basis of preferred embodiments and with reference to the accompanying drawings:

BRIEF DESCRIPTION OF THE DRAWINGS

FIG. 3A shows the tool holding/releasing device of FIG. 1 as well as the treatment tool supported in it in a retracted position.

FIG. 3B shows the tool holding/releasing device of FIG. 1 as well as the treatment tool supported in it in an extended position.

FIG. 3C shows the tool holding/releasing device of FIG. 1 as well as the treatment tool with the tool holding/releasing device being ready for insertion or removal of the treatment tool.

FIG. 3D shows the tool holding/releasing device of FIG. 1 without a treatment tool.

DESCRIPTION OF PREFERRED EMBODIMENTS

Figure 1:
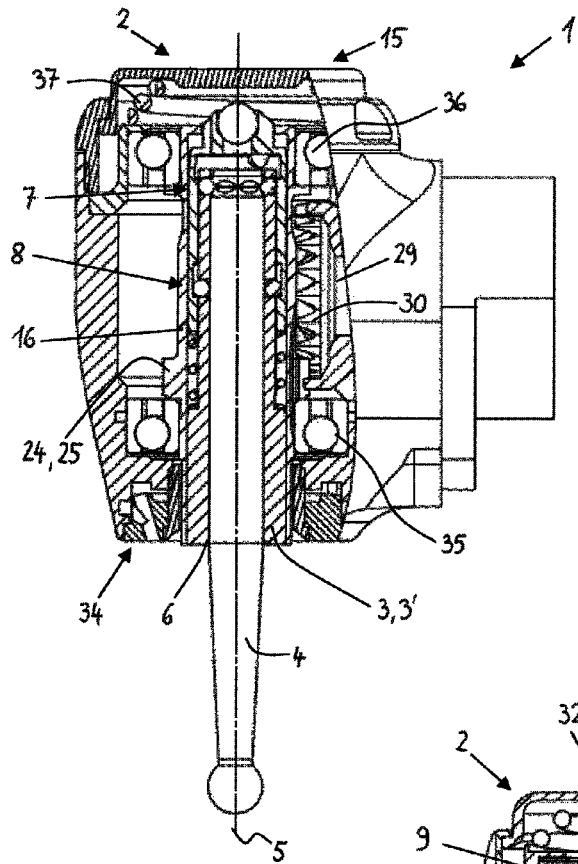
FIG. 1 shows a first embodiment of a mechanically driven medical handpiece with a tool holding/releasing device that has a first and a second separate holding unit for the tool.
Figure 2:
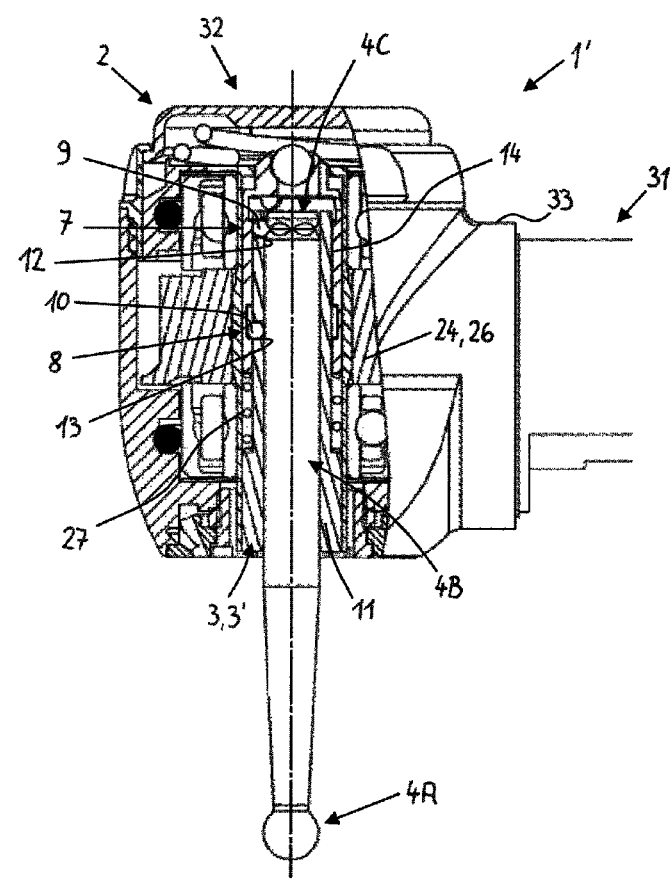
FIG. 2 shows a second embodiment of a fluid-driven medical handpiece with a tool holding/releasing device that has a first and a second separate holding unit for the tool.

FIGS. 1 and 2 show two medical or dental handpieces 1, 1' that differ in the type of drive: Handpiece 1 is implemented as a mechanically driven handpiece whose hollow shaft 3 for the support of a treatment tool 4 can be put in motion, particularly rotary motion, using a mechanical drive train. The mechanical drive train comprises at least a shaft 29, which has a gearwheel 30 on one end that engages in a drive element 24 implemented as a gearwheel or pinion gear 25 connected to hollow shaft 3. The shaft 29 is or can be directly or indirectly connected to a motorised drive which generates a drive motion that can be transmitted via shaft 29, gearwheel 30 and drive element 24 onto the hollow shaft 3.

Handpiece 1' is implemented as a fluid-driven, particularly a compressed gas-driven, handpiece, in which the hollow shaft 3 for the accommodation of a treatment tool 4 is connected to a drive element 24 implemented as a rotor or impeller 26. The rotor 26 is supplied with a fluid and thereby placed in motion together with hollow shaft 3.

Of course, the drive element 24 can also be implemented differently, for example as part of an eccentric drive, or as a shaft transmitting vibrations, or as a drive element for the transmission of sawing motions.

The following description refers to both handpieces 1, 1' and to components that are substantially identical in both handpieces 1, 1'.

The handpieces 1, 1' are designed as so-called contra-angle handpieces whose outer shell 33 has a handle section 31 and a head section 32. The outer shell 33 can be single-part or multi-part. In or on head section 32, among other things there are a tool holding/releasing device 2, the drive element 24 and a device 34 for the release of a fluid or a fluid/compressed gas mixture.

The tool support/release device 2 comprises the hollow shaft 3, which extends along a central axis 5 through the head section 32. The central axis 5 runs perpendicular to the handle section 31, in particular at about right angles to the handle section 31. If the hollow shaft 3 is supported rotatably in the handpiece 1, 1' so that it can rotate, the central axis 5 is preferably identical to the axis of rotation of hollow shaft 3. In hollow shaft 3, a treatment tool 4 can be inserted releasably, for example a drill, a saw or a file. Hollow shaft 3 is implemented as a hollow cylindrical, single-part shaft 3' whose inner diameter is substantially constant over its entire length. On one end, the hollow shaft 3 has a tool receptacle opening 6 that ends at an opening in outer shell 33 or passes through it. Through these two openings, a treatment tool 4 can be inserted in a releasable manner into hollow shaft 3 and thus into the head section 32 of handpiece 1, 1', and/or removed from it.

Hollow shaft 3 is connected in a rotationally fixed manner to a bearing sleeve 16, for example by pressing and/or by welding and/or by gluing. One or more bearings are placed on bearing sleeve 16, for example roller bearings, particularly two ball bearings 35, 36, so that bearing sleeve 16 and all components directly or indirectly connected to bearing sleeve 16, particularly the hollow shaft 3 and a locking sleeve 14 that will be described below, can be moved and particularly rotated relative to outer shell 33.

On hollow shaft 3, as a part of the tool holding/releasing device 2, there are provided a first holding unit 7 and a second holding unit 8, wherein each of the two holding units 7, 8 is designed to secure a treatment tool 4 held in the hollow shaft 3 axially in hollow shaft 3 and to transmit a torque transmitted from drive element 24 to treatment tool 4. Each of the two holding units 7, 8 is preferably designed to effect the axial holding of the treatment tool 4 and the transmission of torque independently of the other holding unit 7, 8. Furthermore, it is preferable for each of the two holding units 7, 8 to be designed to effect the axial holding of the treatment tool 4 and transmission of the torque alone, that is, each holding unit 7, 8 secures the treatment tool 4 axially and transmits the torque to treatment tool 4 without the significant assistance of the other holding unit 7, 8. This can easily be seen in particular from FIG. 3B, where the axial holding of and transmission of torque into treatment tool 4 takes place exclusively using the second holding unit 8. However, the same applies to FIG. 3A, in which the first holding unit 7 axially secures the treatment tool and transmits torque to treatment tool 4. The axial holding of the treatment tool 4 is understood to mean that the treatment tool 4 is supported or attached firmly in hollow shaft 3 in such a way that it does not slide along the central axis 5 out of hollow shaft 3 alone and/or unintentionally.

Each of the two holding units 7, 8 has at least one, preferably several, shaped elements 9, 10, and one, preferably several, bores 12, 13 penetrating the outer wall 11 of the hollow shaft 3, in which the at least one shaped element 9, 10 can be held in such a way that it projects through the bore 12, 13 into the interior of hollow shaft 3. The shaped elements 9, 10 are preferably designed as balls. The bores 12, 13 are preferably implemented as cross-holes (relative to the central axis 5) that particularly penetrate the outer jacket 11 of the cylindrically shaped hollow shaft 3. The bores 12, 13 are designed in such a way that a part of the shaped elements 9, 10 projects into the interior of the hollow shaft 3, but that the entire shaped element 9, 10 does not extend through the bores 12, 13 into the interior of the hollow shaft 3. This is achieved, for example, in that the bores 12, 13 narrow somewhat towards the central axis 5 or the diameter (parallel to the central axis 5) of the bores 12, 13 is reduced somewhat in the direction of the central axis 5. The diameter of the bores 12, 13 is thus smaller in the area of the bores 12, 13 facing the central axis than the diameter of the shaped elements 9, 10. In contrast, the diameter of the bores 12, 13 at the opening of the bores 12, 13 facing the locking sleeve 14 is as large as or larger than the diameter of the shaped elements 9, 10.

In the mechanically driven handpiece 1 in FIG. 1, for each holding unit 7, 8 there are provided six shaped elements 9, 10 and six bores 12, 13. In the fluid-driven handpiece 1' in FIG. 2, for each holding unit 7, 8 there are provided three shaped elements 9, 10 and three bores 12, 13.

Between the hollow shaft 3 and bearing sleeve 16, particularly in a ring groove between the hollow shaft 3 and bearing sleeve 16, the locking sleeve 14 is located. The locking sleeve 14, preferably also implemented as a hollow cylinder, surrounds the hollow shaft 3 and can move relative to the hollow shaft 3, in particular it is able to slide along the central axis 5. The locking sleeve 14 is tensioned by a spring element 27, particularly a spiral spring, away from the tool receptacle opening 6 or towards an operating element 15 for releasing the treatment tool 4 from the hollow shaft 3. The spring element 27 is supported on a shoulder 28 provided on the outside of the hollow shaft 3 (see FIG. 3B). Adjacent to shoulder 28, the wall thickness of the jacket of hollow shaft 3 is greater than in the area of the two holding units 7, 8. In the area with the greater wall thickness, the hollow shaft 3 is connected directly to the bearing sleeve 16.

The locking sleeve 14 has a first recess 17 on its inner side facing the central axis, which is located in the vicinity of the first holding unit 7 and/or is assigned to the first holding unit 7. The locking sleeve 14 furthermore has a second recess 18 which is located in the vicinity of the second holding unit 8 and/or is assigned to the second holding unit 8. The recesses 17, 18 are thus arranged and dimensioned in such a way that the at least one shaped element 9 of the first holding element 7 can be held in the first recess 17 and at least one shaped element 10 of the second holding unit 8 can be held in the second recess 18. The depth of the recesses 17, 18 is such that when a shaped element 9, 10 is at least partly held or accommodated in them, shaped element 19, 10 projects into the hollow shaft 3 to a lesser extent, or not at all. If a shaped element 9, 10 is not held in a recess 17, 18, but rather contacts an inner wall section 38A, 38B of the locking sleeve 14 that is adjacent to a recess 17, 18, then the shaped element 9, 10 projects into the hollow shaft 3 or further into the hollow shaft 3. The recesses 17, 18 are preferably implemented as ring grooves or arcs running along the inner side of the locking sleeve 14.

Each of the recesses 17, 18 has a shoulder 19, 21 located closer to the tool receptacle opening 6 and a shoulder 20, 22 located further from the tool receptacle opening 6 (see FIGS. 3A and 3C). The distance between the two shoulders 19, 21 of the two recesses 17, 18 located closer to the tool receptacle opening 6 is greater than the distance between the center point of the at least one shaped element 9 of the first holding unit 7 and the center point of the at least one shaped element 10 of the second holding unit 8. The difference between the distance between the two shoulders 19, 21 and the distance between the center points of the two shaped elements 9, 10, is, for example, about 0.3 to about 1.0 mm, preferably about 0.4 to about 0.5 mm. The distance between the two shoulders 19, 21, for example, is about 2.0 to about 4.0 mm, and the distance between the center points of the two shaped elements 9, 10 is, for example, about 1.5 to about 3.5 mm.

The diameter D17 (running perpendicular to the central axis 5) of the first recess 17, which is located further away from the tool receptacle opening 6 than the second recess 18, is less than the diameter D18 (running perpendicular to the central axis 5) of the second recess 18. Due to the smaller diameter D17, the shaped elements 9 are moved closer to the central axis 5 or project further into the interior of the hollow shaft 3. Thus the shaped element or elements 9 of the first recess 17 additionally form an axial stop for the treatment tool 4 and/or for a shoulder provided in the end area of the shaft section 4B of the treatment tool 4 (see FIG. 3A). The difference between the two diameters D17, D18 preferably lies in a range of about 0.25 to about 0.05 mm, particularly about 0.1 mm. The diameter D17 of the first recess 17, for example, is about 2.3 to about 2.6 mm, preferably about 2.5 mm. The diameter D18 of the second recess 18, for example, is about 2.4 to about 2.7 mm, preferably about 2.6 mm.

Furthermore, the two recesses 17, 18 have axial heights H17, H18 relative to the central axis 5 of different size. Preferably the axial height H17 of the first recess 17 located further from the tool receptacle opening 6 is less than the axial height H18 of the second recess 18 located closer to the tool receptacle opening 6. The heights H17, H18 of the two recesses 17, 18 are for example about 0.5 to about 1.5 mm; the difference between the two heights H17, H18 is for example 0.2 to about 0.5 mm.

The locking sleeve 14 has an extension or a protrusion 24 on its end facing the operating element 15 that projects through an opening 23 in bearing sleeve 16 (see particularly FIG. 3D). The extension 24 has a spherical end 25, which is implemented either as an integral part of the locking sleeve 14 or as a separate component, for example a ball or half-ball, which is connected to the extension 24, for example pressed into a seat or held in such a manner that it can rotate. The spherical end 25 serves as a contact, particularly substantially only a point-shaped contact, with the operating element 15, by which the user can slide the locking sleeve 14 and thus fasten a treatment tool 4 into the hollow shaft and/or remove it.

The operating element 15, for example designed as a pressure cap or pressure cover, is tensioned by a spring element 37, particularly by a spiral spring (see FIG. 1) and is attached to the head section 32 of handpiece 1, 1' in such a way that it can slide, particularly relative to the hollow shaft 3, to the locking sleeve 14 and to the bearing sleeve 16. If the operating element 15 is moved against the spring force of spring element 37 towards the locking sleeve 14, it contacts the spherical end 25 of the locking sleeve 14 and furthermore pushes the locking sleeve 14 against the spring force of the spring element 27. If the operating element 15 is released, the two spring elements 27, 37 push the locking sleeve 14 and/or the operating element 15 automatically back into the starting position shown in FIG. 1. Preferably, the operating element 15 has a protrusion on its inner side opposite the spherical end 25 and by means of which contact can be made with the spherical end 25.

A preferred design of a treatment tool 4, that can be connected to the handpiece 1, it and can be inserted into the tool holding/releasing device 2, is shown for example in FIG. 2. The treatment tool 4 comprises a treatment section 4A and a shaft section 4B. The treatment section 4A is designed to contact a treatment site for the removal of material or tissue and is equipped with blades or cutters. The shaft section 4B is used to connect to the handpiece 1, 1'. At least a part of the shaft section 4B is preferably implemented in a cylindrical form. On shaft section 4B there is preferably provided a single contact element 4C for selective contact with the at least one shaped element 9, 10 of the first holding unit 7 or the second holding unit 8. Especially preferable the location of the contact element 4C is directly at that end of the shaft section 4B that is furthest from the treatment section 4A. The contact element 4C comprises, for example, at least one receptacle, a recess, a ring groove or a depression for the engagement of at least one shaped element 9, 10. The contact element 4C may, for example, surround the shaft section 4B in a ring shape or in a semicircle and/or may have cups. The part of the shaft section 4B that connects to the only contact element 4C, extends in the direction of the treatment section 4A and can be supported in hollow shaft 3 has a substantially constant outer diameter.

FIGS. 3A-3D show the chucking device 2A, which is part of the tool holding/releasing device 2. FIG. 3A shows the treatment tool 4 in its retracted position, in which it projects less from the handpiece 1, 1' and/or from the tool holding/releasing device 2. The axial holding and torque transmission of the treatment tool 4 is undertaken by the first holding unit 7, whose shaped elements 9 emerge from the first recess 17 and are forced by an inner wall section 38B of the locking sleeve 14 (see FIG. 3B) adjacent to the recess 17 into the interior of hollow shaft 3, where they engage the contact element 4C of the treatment tool 4. The shaped elements 10 of the second holding unit 8 are at least partly held in the second recess 18 and contact the shaft section 4B of the treatment tool 4 only slightly or not at all, particularly only at one contact point. Furthermore, it is noticeable that the shoulder 21 of the second recess 18 that is closer to the tool receptacle opening 6 contacts the shaped elements 10, so that the shaped elements 10 serve as a stop for the shoulder 21 and limit the movement of the locking sleeve 14 in the direction of the operating element 15. The height H18 of the second recess 18 is preferably dimensioned so that the shoulder 21 stops at the shaped elements 10 without the locking sleeve 14 contacting the bearing sleeve 16 with its side facing the operating element 15, so that between the locking sleeve 14 and the bearing sleeve 16 a small open space 39 occurs and/or the protrusion 24 of the of the locking sleeve 14 does not project from opening 23 with its maximum possible length.

FIG. 3B shows the treatment tool 4 in its extended position, in which it projects far from the handpiece 1, 1' and/or from the tool holding/releasing device 2. The axial holding and torque transmission of the treatment tool 4 is carried out by the second holding unit 8, whose shaped elements 10 emerge from the second recess and are forced by an inner wall section 38A of the locking sleeve 14 adjacent to the recess 18 into the interior of hollow shaft 3, where they engage the contact element 4C of the treatment tool 4. The shaped elements 9 of the first holding unit 7 are also forced by an inner wall section 38B of the locking sleeve 14 adjacent to the recess 18 into the interior of hollow shaft 3, which is however empty in this area, that is, in which no part of the shaft section 4B of the treatment tool 4 is located. In this position, the locking sleeve 14, with its side facing the operating element 15, contacts the inner side of the bearing sleeve 16 and the protrusion 24 of the locking sleeve 14 projects out of opening 23 with its maximum possible length.

FIG. 3C shows a situation in which the treatment tool 4 is inserted into or removed from the tool holding/releasing device 2. Using operating element 15, the locking sleeve 14 is pushed against the spring force of the spring element 27 into the bearing sleeve 16 or in the direction of the tool receptacle opening 6. The shaped elements 9, 10 of the two holding units 7, 8 are at least partly held in their recesses 17, 18 in the locking sleeve 14, contact the shaft section 4B of the treatment tool 4 only slightly or not at all, and in particular to not engage contact element 4C of the treatment tool 4, so that the shaft section 4B of the treatment tool 4 can move in the hollow shaft 3 without great resistance.

In particular in FIGS. 3A and 3B it can therefore be seen that the handpieces 1, 1' or the tool holding/releasing device 2, that is, in particular the holding units 7, 8 and the locking sleeve 14 are designed in such a way that the treatment tool 4 can be fastened into the hollow shaft 3 at different insertion depths, wherein the insertion depths (that is, the position of the treatment tool 4 in the hollow shaft 3 or the length of the part of treatment tool 4 projecting out of handpiece 1, 1') are predetermined or defined by the holding units 7, 8. It can furthermore be seen that the handpieces 1, 1' or the tool holding/releasing device 2, that is in particular the holding units 7, 8 and the locking sleeve 14 are designed in such a way that the axial holding of the treatment tool 4 and the transmission of torque are only carried out by one of the two holding units 7, 8, that is, that only one of the two holding units 7, 8 holds the treatment tool 4 axially and transmits the torque into the treatment tool 4 without the significant assistance of the other holding unit 7, 8.

The scope of protection is not limited to the embodiments described herein but instead comprises all embodiments which employ or include the basic appropriate functional principles. In addition, all features of all the embodiments described and illustrated herein may be combined with one another. It is thus in particular possible to equip the tool holding/releasing device 2 with more than two holding units 7, 8, so that the treatment tool 4 can be fastened at more than two different insertion depths in hollow shaft 3. Furthermore, the locking sleeve 14 and the spring element 27 can be arranged in the sense of a kinetic reversal in such a way that the locking sleeve 14 is tensioned in the direction of the tool receptacle opening 6 or away from the operating element 15.

What is claimed is:

1. A medical or dental handpiece comprising:
   a tool holding/releasing device with a hollow shaft for holding a treatment tool that can be placed in a drive movement, wherein the hollow shaft extends along a central axis and has a tool receptacle opening;
   a mechanical or fluid driven drive configured to drive the hollow shaft for holding a treatment tool;
   a first holding unit and a second holding unit separate from the first holding unit, the second holding unit being offset axially from the first holding unit with respect to the central axis, wherein each holding unit is designed to secure a treatment tool supported in the hollow shaft axially and to transmit a torque to the treatment tool, the first holding unit and the second holding unit being configured to hold the treatment tool at different insertion depths, and wherein each holding unit comprises at least one shaped element and a bore penetrating the outer wall of the hollow shaft, in which the at least one shaped element can be held in such a way that it projects through the bore into the interior of the hollow shaft;
   a locking sleeve operatively coupled to each at least one shaped element that can move relative to the hollow shaft and that surrounds the hollow shaft; and
   an operating element operatively connected to the locking sleeve for the movement or sliding of the locking sleeve, wherein
   the locking sleeve is movable at least in an axial direction relative to the hollow shaft to move the holding units into an operating position in which the at least one shaped element of the first holding unit is moved towards the central axis and in which the at least one shaped element of the second holding unit is moved away from the central axis to hold the treatment tool at a selected one of the different insertion depths.

2. The medical or dental handpiece according to claim 1, wherein the hollow shaft is configured to have a hollow, cylindrical, single-part shaft wand having an inner diameter substantially constant along an entire length of the shaft.

3. The medical or dental handpiece according to claim 1, wherein the locking sleeve has a first recess on its inner side which is associated with the first holding unit and a second recess which is associated with the second holding unit, so that the at least one shaped element of the first holding unit can be held in the first recess and the at least one shaped element of the second holding unit can be held in the second recess.

4. The medical or dental handpiece according to claim 3, wherein the first recess has a first shoulder located closer to the tool receptacle opening and a second shoulder located more distant from the tool receptacle opening, that the second recess has a third shoulder located closer to the tool receptacle opening and a fourth shoulder located more distant from the tool receptacle opening, and that the distance between the first and third shoulders is greater than the distance between the center point of the at least one shaped element of the first holding unit and the center point of the at least one shaped element of the second holding unit.

5. The medical or dental handpiece according to claim 3 wherein the first recess is located further from the tool receptacle opening than the second recess, wherein the diameter of the first recess is less than the diameter of the second recess.

6. The medical or dental handpiece according to claim 3, wherein the axial height of the two recesses relative to the central axis is different, wherein the axial height of the first recess located further from the tool receptacle opening is less than the axial height of the second recess located closer to the tool receptacle opening.

7. The medical or dental handpiece according to claim 1, wherein the hollow shaft and the locking sleeve are surrounded by a bearing sleeve that has an opening on one end facing the operating element through which contact can be made between the locking sleeve and the operating element.

8. The medical or dental handpiece according to claim 7, wherein a protrusion of the locking sleeve projects through the opening of the bearing sleeve.

9. The medical or dental handpiece according to claim 8, wherein the protrusion of the locking sleeve has a spherical end facing the operating element, with which a substantially point-shaped contact can be achieved with the operating element.

10. The medical or dental handpiece according to claim 7, wherein a drive element is provided on the bearing sleeve in order to place the hollow shaft in a drive motion.

11. The medical or dental handpiece according to claim 1, wherein the locking sleeve is tensioned by a spring element that is supported on a shoulder located on the outer side of the hollow shaft or a shoulder located on an inner side of the bearing sleeve.

12. The medical or dental handpiece according to claim 1, wherein the at least one shaped element of the first holding unit or the second holding unit is spherical or comprises a spherical end that faces the central axis of the hollow shaft.

13. The medical or dental handpiece according to claim 1, wherein the first holding unit and the second holding unit each comprise three or six shaped elements.

14. The medical or dental handpiece according to claim 1, comprising a treatment tool that has a treatment section and a shaft section, on which a single contact element is provided to selectively receive at least one shaped element of the first holding unit or the second holding unit, wherein the contact element is located directly at that end of the shaft section that is furthest away from the treatment section.

15. The medical or dental handpiece according to claim 14, wherein the shaft section extending distally away from the single contact element and towards the treatment section has a substantially constant outer diameter.

16. A medical or dental handpiece comprising:
   a tool holding/releasing device with a hollow shaft for holding a treatment tool that can be placed in a drive movement, wherein the hollow shaft extends along a central axis and has a tool receptacle opening;
   a bearing sleeve that surrounds the hollow shaft;
   a mechanical or fluid driven drive configured to drive the hollow shaft by driving the bearing sleeve;
   a first holding unit and a second holding unit separate from the first holding unit, the second holding unit being offset axially from the first holding unit with respect to the central axis, wherein each holding unit is designed to secure a treatment tool supported in the hollow shaft axially and to transmit a torque to the treatment tool, and wherein each holding unit comprises at least one shaped element and a bore penetrating the outer wall of the hollow shaft, in which the at least one shaped element can be held in such a way that it projects through the bore into the interior of the hollow shaft;

a locking sleeve operatively coupled to the shaped elements and positioned between the bearing sleeve and hollow shaft, wherein the locking sleeve is movable in at least an axial direction between the bearing sleeve and the hollow shaft; and an operating element operatively connected to the locking sleeve for the movement of the locking sleeve, wherein the first holding unit and the second holding unit are configured to selectively hold the treatment tool at different insertion depths.

17. The medical or dental handpiece according to claim 16, wherein the locking sleeve has a first recess on its inner side which is associated with the first holding unit and a second recess which is associated with the second holding unit and is axially offset from the first recess, so that the at least one shaped element of the first holding unit can be held in the first recess and at least one shaped element of the second holding unit can be held in the second recess.

18. The medical or dental handpiece according to claim 17, wherein the first recess has a first shoulder located closer to the tool receptacle opening and a second shoulder located more distant from the tool receptacle opening, that the second recess has a third shoulder located closer to the tool receptacle opening and a fourth shoulder located more distant from the tool receptacle opening, and that the distance between the first and third shoulders is greater than the distance between the center point of the at least one shaped element of the first holding unit and the center point of the at least one shaped element of the second holding unit.

19. The medical or dental handpiece according to claim 17 wherein the first recess is located further from the tool receptacle opening than the second recess, wherein the diameter of the first recess is less than the diameter of the second recess.

20. The medical or dental handpiece according to claim 17, wherein the axial height of the two recesses relative to the central axis is different, wherein the axial height of the first recess located further from the tool receptacle opening is less than the axial height of the second recess located closer to the tool receptacle opening.

21. The medical or dental handpiece according to claim 16, wherein the bearing sleeve has an opening on one end facing the operating element through which contact can be made between the locking sleeve and the operating element.

22. The medical or dental handpiece according to claim 16, wherein the locking sleeve is tensioned by a spring element that is supported on a shoulder located on the outer side of the hollow shaft or a shoulder located on an inner side of the bearing sleeve.

23. A medical or dental handpiece comprising:

a tool holding/releasing device with a hollow shaft for holding a treatment tool that can be placed in a drive movement, wherein the hollow shaft extends along a central axis and has a tool receptacle opening;

a bearing sleeve that surrounds the hollow shaft and comprises a drive element;

a mechanical or fluid driven drive configured to drive the hollow shaft by drivingly engaging the drive element of the bearing sleeve;

a first holding unit and a second holding unit separate from the first holding unit, the second holding unit being offset axially from the first holding unit with respect to the central axis, wherein each holding unit is designed to secure a treatment tool supported in the hollow shaft axially and to transmit a torque to the treatment tool, and wherein each holding unit comprises at least one shaped element and a bore penetrating the outer wall of the hollow shaft, in which the at least one shaped element can be held in such a way that it projects through the bore into the interior of the hollow shaft;

a locking sleeve operatively coupled to the shaped elements that can move relative to the hollow shaft and the bearing sleeve; and an operating element operatively coupled to the locking sleeve to move the locking sleeve, wherein the bearing sleeve has an opening on one end facing the operating element through which the operating element can be extended to contact the locking sleeve.

24. The medical or dental handpiece according to claim 23, wherein a protrusion of the locking sleeve projects through the opening of the bearing sleeve.

25. The medical or dental handpiece according to claim 24, wherein the protrusion of the locking sleeve has a spherical end facing the operating element, with which a substantially point-shaped contact can be achieved with the operating element.

26. The medical or dental handpiece according to claim 23, wherein a drive element is provided on the bearing sleeve in order to place the hollow shaft in a drive motion.

27. The medical or dental handpiece according to claim 23, wherein the locking sleeve is tensioned by a spring element that is supported on a shoulder located on the outer side of the hollow shaft or a shoulder located on an inner side of the bearing sleeve.

28. The medical or dental handpiece according to claim 23, wherein the locking sleeve has a first recess on an inner side which is associated with the first holding unit and a second recess which is associated with the second holding unit and is axially offset from the first recess, so that the at least one shaped element of the first holding unit can be held in the first recess and at least one shaped element of the second holding unit can be held in the second recess.

29. The medical or dental handpiece according to claim 28, wherein the first recess has a first shoulder located closer to the tool receptacle opening and a second shoulder located more distant from the tool receptacle opening, that the second recess has a third shoulder located closer to the tool receptacle opening and a fourth shoulder located more distant from the tool receptacle opening, and that the distance between the first and third shoulders is greater than the distance between the center point of the at least one shaped element of the first holding unit and the center point of the at least one shaped element of the second holding unit.

30. The medical or dental handpiece according to claim 28 wherein the first recess is located further from the tool receptacle opening than the second recess, wherein the diameter of the first recess is less than the diameter of the second recess.

31. The medical or dental handpiece according to claim 28, wherein the axial height of the two recesses relative to the central axis is different, wherein the axial height of the first recess located further from the tool receptacle opening is less than the axial height of the second recess located closer to the tool receptacle opening.

* * * * *